(12) United States Patent
Huang

(10) Patent No.: US 6,183,252 B1
(45) Date of Patent: Feb. 6, 2001

(54) DENTAL SYRINGE FOR DENTISTS

(76) Inventor: Wen-Shan Huang, No. 25, Alley 9, Lane 10, Da-Jen St., Chungho City, Taipei Hsien (TW)

(*) Notice: Under 35 U.S.C. 154(b), the term of this patent shall be extended for 0 days.

(21) Appl. No.: 09/450,612

(22) Filed: Nov. 30, 1999

(51) Int. Cl.[7] .................................................. A61C 17/00
(52) U.S. Cl. ............................................. 433/80; 433/127
(58) Field of Search ............................. 433/80, 126, 127, 433/128

(56) References Cited

U.S. PATENT DOCUMENTS

| | | | |
|---|---|---|---|
| 3,393,676 | * | 7/1968 | Kummer et al. ........................ 433/80 |
| 5,125,835 | * | 6/1992 | Young ..................................... 433/80 |
| 5,306,146 | * | 4/1994 | Davis et al. ............................ 433/80 |
| 5,433,485 | * | 7/1995 | Austin, Jr. et al. .................... 433/80 |
| 5,490,683 | * | 2/1996 | Mickel et al. ......................... 433/128 |

* cited by examiner

Primary Examiner—John J. Wilson
(74) Attorney, Agent, or Firm—William E. Pelton, Esq.

(57) ABSTRACT

A dental syringe for dentists, especially a holding means thereof for holding a nozzle, is disclosed. The holding means has a rear tube threadingly engaging with a head of the dental syringe, and a front tube threadingly engaging with the rear tube. An inner barrel is slidably contained in the front and the rear tube, and an outer barrel slidably covers the tubes. A nozzle can be inserted into the inner tube and after a nib thereof, whose diameter is smaller than the nozzle itself, extends through a central opening defined in the bottom of the inner tube. A plurality of balls, formerly blocked by the outer surface of the inner tube, falls and engages with a circular groove defined in the nozzle thus securely fixing the nozzle there. At this time the outer barrel is pushed forward by a spring to press the balls. By pulling the outer barrel backward, the pressing will be released and the balls will be pushed back by the front rim of the inner barrel under the force of another spring. The nozzle can now be removed from the holding means. The dental syringe for dentists is easy to operate with two hands and will not pinch a dentist's gloves or hands.

5 Claims, 6 Drawing Sheets

DENTAL SYRINGE FOR DENTISTS

BACKGROUND OF THE INVENTION

1. Field of the Invention

The invention relates to a dental syringe for dentists, especially to a dental syringe of which the nozzle can be easily fitted and removed, and a nozzle-holding means with which the glove or even the fingertip of the dentist will not be liable to be pinched.

2. Description of Related Art

Dentists often use a drill to grind and clean the cavities in teeth, and use a dental syringe, containing either water or gas, to flush or blow away the bits produced by the drilling.

Shown in FIGS. 5 and 6 is a conventional dental syringe (2) for dentists, consisting of a head (21), a handle (22), a holding device (23), and a nozzle (24). The nozzle (24) includes a first end, and a second end with a circumferential under cut defined near thereto. The nozzle (24) has a major diameter and the under cut has a minor diameter. The head (21) has a male thread (211) thereunder used to engage with a female thread (221) defined in the top of the handle (22). In use, the first end of the nozzle (24) can be inserted in a patient's mouth to align with a cavity needed to be flushed. For reasons of hygiene, the nozzle (24) must be changed usually at least once for each patient. The second end of the nozzle (24) is affixed to the head (21) by means of the holding device (23) received in an opening (212) defined in the front of the head (21). The holding device (23) includes a pipe (231) having a male thread for engaging with a female thread defined in the opening (212), a small barrel (232) covering and being slidable along the pipe (231), and a spring (233) being pressed between a bottom of the barrel (232) and a bottom of the opening (212). In a non-retracted mode of the dental syringe, the barrel (232) is pushed away from the head (21) by the spring (233) and covers a plurality of balls disposed in the pipe (232) thus pressing them radiallyinward to a first position. The balls in the first position describe a diameter that is equal to the minor diameter but smaller than the major diameter of the nozzle (24) and thus the second end of the nozzle (24) cannot enter the head (21). When the nozzle (24) is to be inserted in the head (21), a dentist must pull the barrel (232) backward against the spring (233) whereafter the balls are free to move to a second position where they describe a diameter greater than the major diameter of the nozzle (24), such that the second end thereof can enter the head (21). Then the dentist releases the barrel (232) which is accordingly pushed back to its original position of the non-retracted mode, thereby urging the balls radially inward to be received in the under cut, whereby the nozzle (24) is securely retained in the head (21). Reversal of the above process enables the nozzle (24) to be removed from the head (21). From the above description, the conventional dental syringe for dentists has following shortcomings:

1. in both assembly and removal, dentists have to simultaneously grasp the nozzle (24), hold the handle (22), and push the barrel (232) which requires considerable dexterity.
2. after releasing the barrel back, a glove or even a hand of the dentist is often pinched between the pipe (24) and the barrel (232).

| THE REFERENCE NUMBERS |
|---|
| 1. dental syringe for dentists |
| 11. head; |
| 110. opening; |
| 111. holding device |
| 112. screw hole; |
| 114. water channel; |
| 116. sink; |
| 118. button; |
| 12. rear tube; |
| 120. rear male thread; |
| 122. front female thread; |
| 124. bottom opening; |
| 126. side air vent; |
| 13. front tube; |
| 130. rear male thread; |
| 132. ball socket; |
| 134. front outer flange; |
| 135. front inner flange; |
| 136. ball; |
| 138. sealing ring; |
| 14. outer barrel; |
| 140. direction groove; |
| 142. mouth; |
| 143. transient portion; |
| 144. direction bar; |
| 146. spring; |
| 15. small barrel; |
| 151. central bottom opening; |
| 152. outer sealing ring; |
| 153. front brim; |
| 154. inner sealing ring; |
| 156. spring; |
| 16. sealing ring; |
| 17. nozzle; |
| 172. circular groove; |
| 174. nib; |
| 176. air vent; |
| 18. handle; |
| 2. dental syringe for dentist; |
| 21. head; |
| 211. male thread; |
| 212. opening; |
| 22. handle; |
| 221. female thread; |
| 23. holding means; |
| 231. pipe; |
| 232. barrel; |
| 233. spring; |
| 234. ball; |
| 24. nozzle. |

DESCRIPTION OF THE PREFERRED EMBODIMENT

Figure 1:
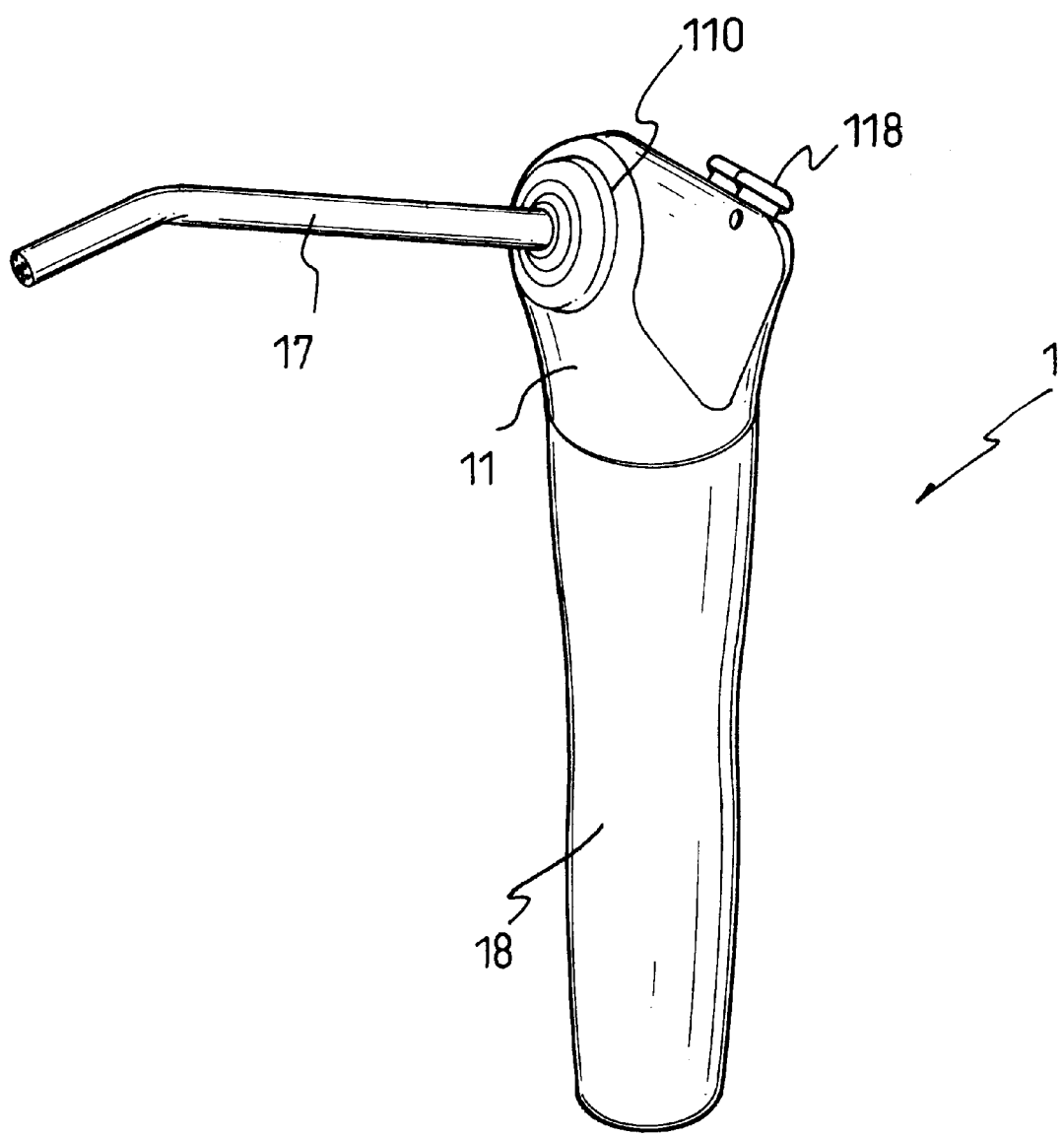
FIG. 1 is a perspective view of the invention.
Figure 2:
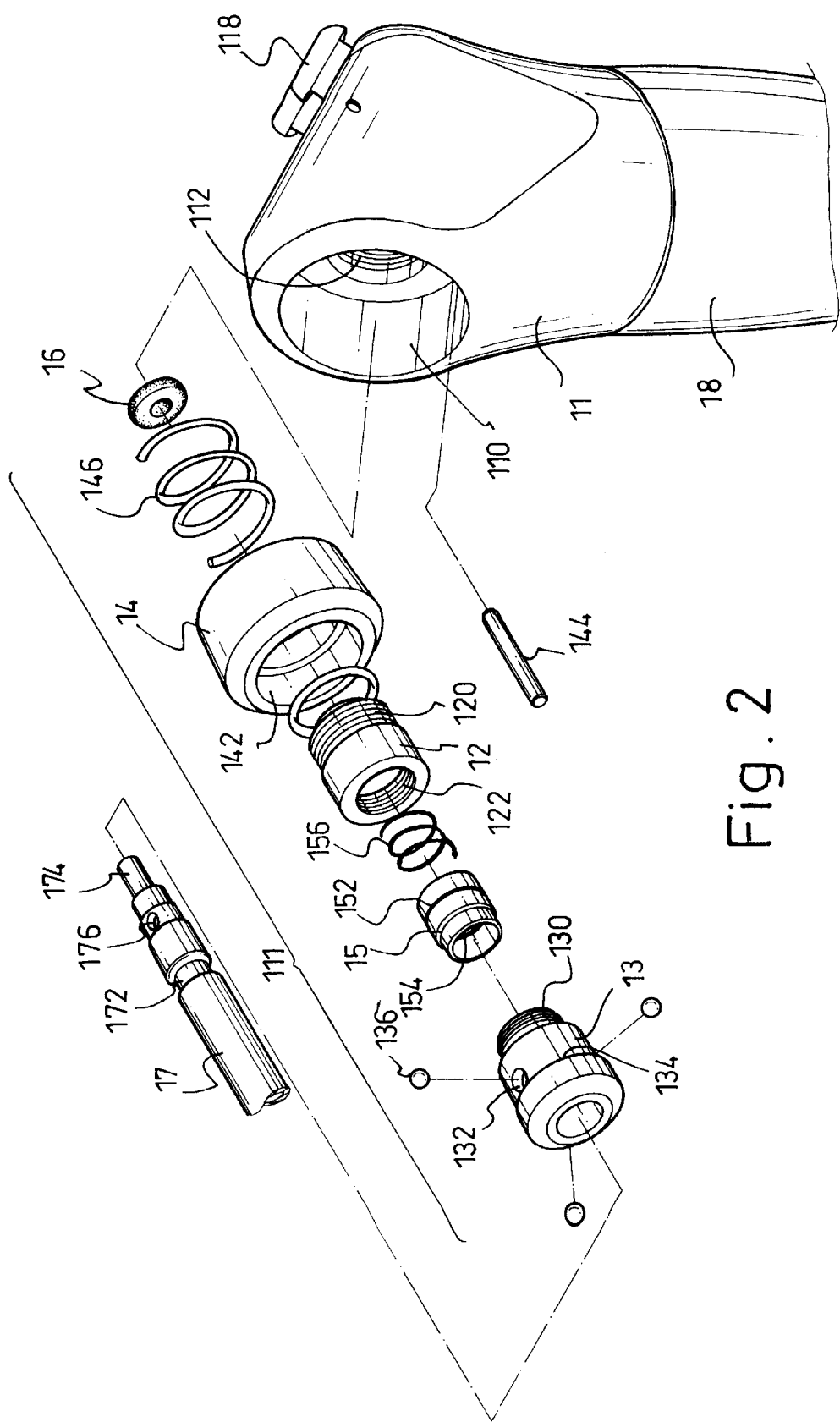
FIG. 2 is a partially exploded view especially showing the holding device of the invention.

As shown in FIGS. 1 and 2, a dental syringe for dentists (1), consists of a head (11), a handle (18) securely affixed on the head (11), a holding device (111) installed in an opening (110) defined in the head (11), a nozzle (17) being able to be inserted in the holding device (111), and a button (118) for operation.

Figure 3:
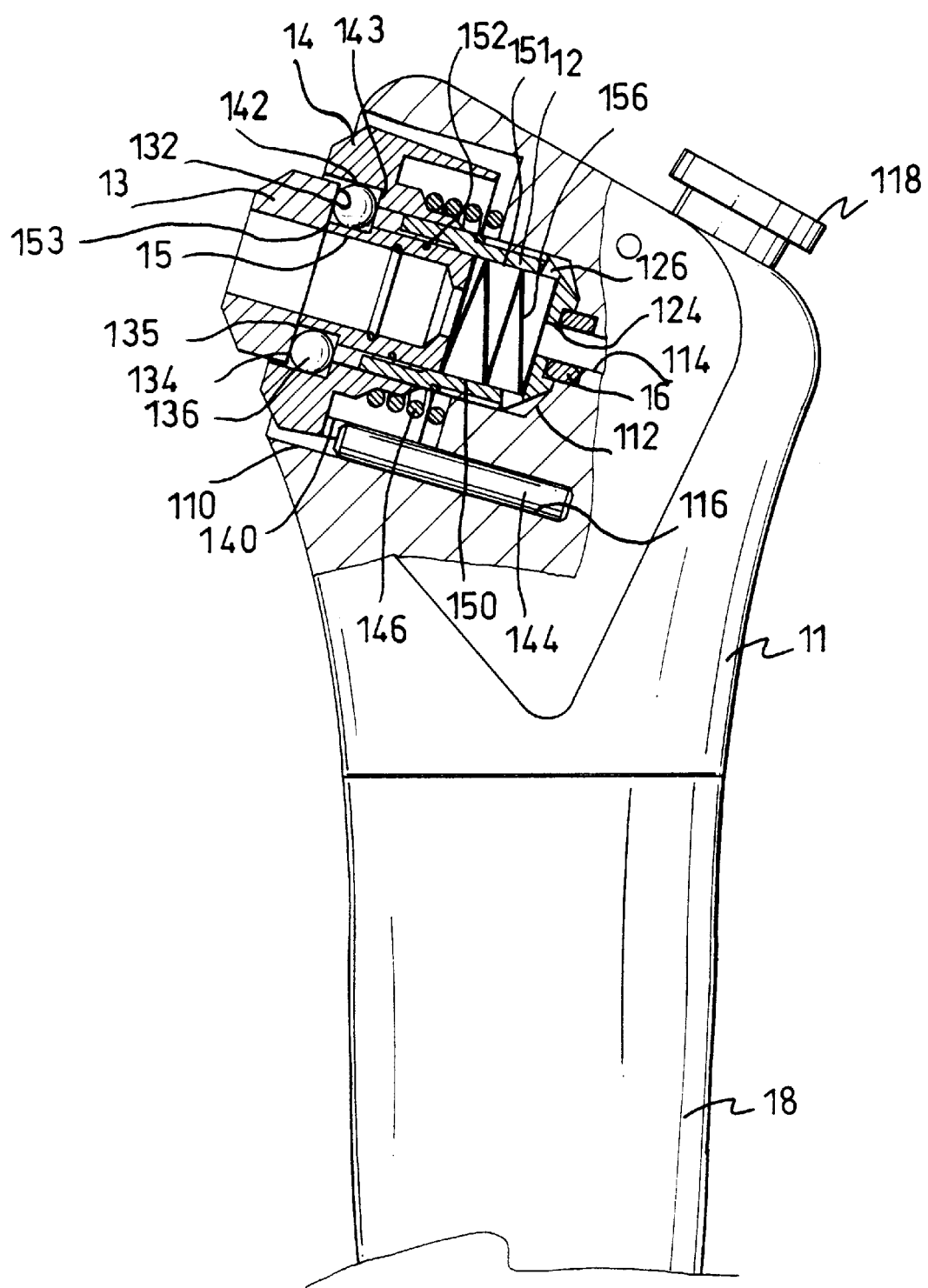
FIG. 3 is a partially cross-sectional view of the invention before the nozzle is inserted.

As shown in the FIGS. 2 and 3, the opening (110) is defined in the head (11) and a threaded hole (112) is defined in communication with a bottom thereof. The threaded hole (112) is further in communication with a water channel (114) in the head (11).

A rear tube (12) includes rear male thread (120) which is threadingly received in the threaded hole (112). The rear tube (12) further includes a front female thread (122), a side air vent (126), and a bottom opening with a diameter smaller than the inner diameter of the rear tube (12). A sealing ring (138) is provided between the rear tube (12) and a face defining the bottom of the opening (110).

A front tube (13) includes a rear male thread (130) which engages with the front female thread (122) of the rear tube (12). The front tube (13) has a front outer flange (134), a front inner flange (135), and a plurality of ball sockets (132) defined in the circumferential wall thereof axially behind the outer and the inner flanges (134, 135). A plurality of balls (136) is accordingly disposed in the plurality of ball sockets (132).

An outer barrel (14) is provided to cover the front and the rear tubes (13, 12). The outer barrel (14) has a front mouth the diameter of which is slightly larger than the inner diameter of the outer barrel (14) and the front outer flange (134) of the front tube (13). A spring (146) is pressed between the bottom of the outer barrel (14) and the face defining the bottom of the opening (110). A direction groove (140) along an axis of the outer barrel (14) is defined in the outer surface of the outer barrel (14) for slidably containing a direction bar (144) formed on the bottom of the opening (110) to ensure that the outer barrel (14) is only able to move along an axis of the opening (110).

An inner barrel (15) is slidably contained in the front and the rear tubes (13, 12), and has a central bottom opening (151), the diameter of which can just allow a nib (174) of the nozzle (17) to extend therethrough. The inner barrel (15) may also have an outer sealing ring (152) provided between the outer surface thereof and the inner surface of the rear tube (12); and/or has an inner sealing ring (154) provided between the inner surface thereof and the nozzle (17). A spring (156) is pressed between the bottoms of the inner barrel (15) and the rear tube (12).

The rear portion of the nozzle (17) has a circular groove (172). The nib (174) has a diameter which is smaller than the outer diameter of the nozzle (17). An air vent (176) is defined in the wall of the nozzle (17) and locates between the circular groove (172) and the nib (174).

Before insertion of the nozzle (17) into the dental syringe (1), a front rim (153) of the inner barrel (15) pushes against the front inner flange (135) of the front tube (13) under the force of the spring (156). The balls (136) are enclosed by the front outer flange (134), the outer surface of the inner barrel (15), the inner surface of a mouth (142) of the outer barrel (14), and a transition portion (143) between the mouth (142) and the inner surface of the outer barrel (14).

Figure 4:
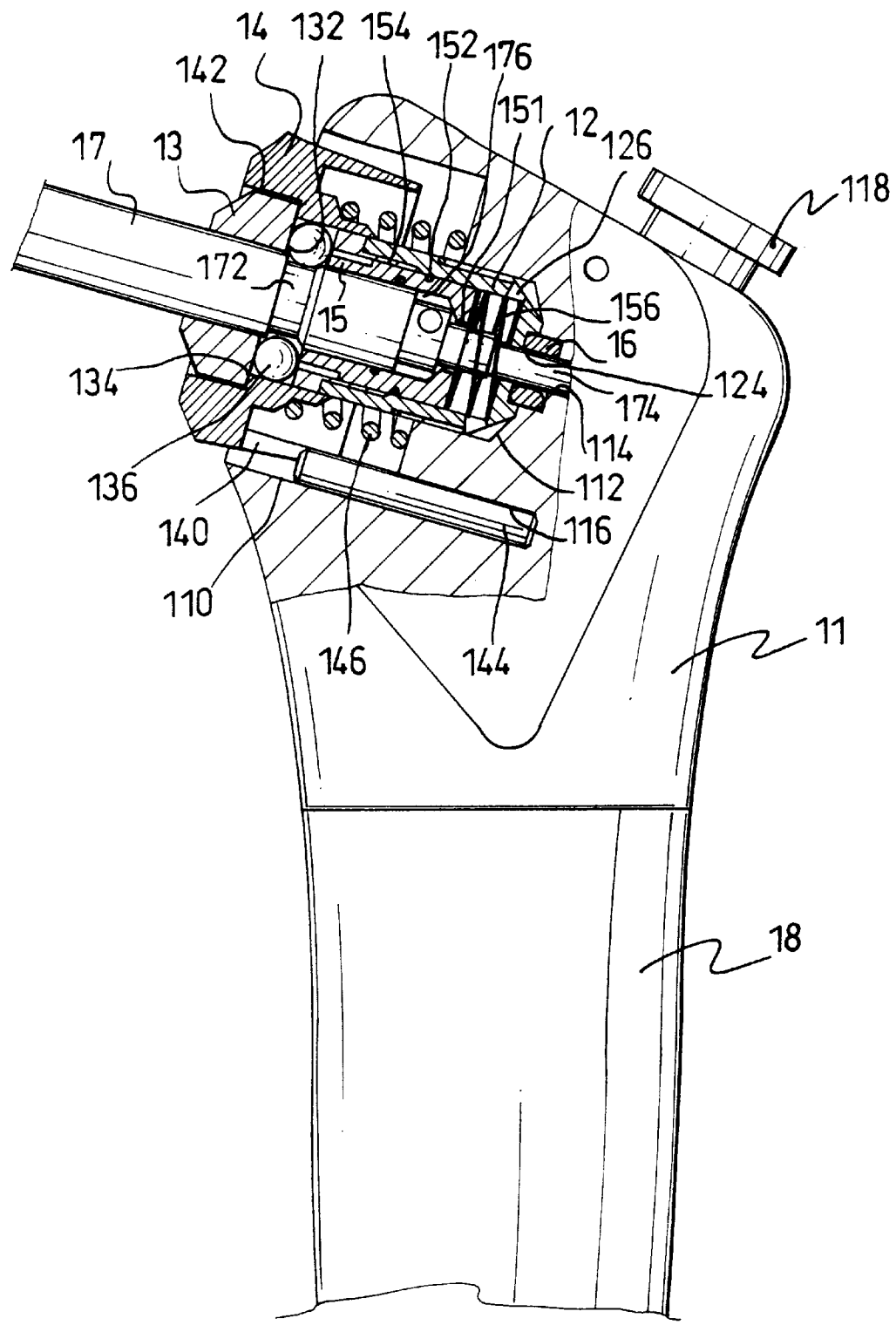
FIG. 4 is a partially cross-sectional view of the invention after the nozzle is inserted.
Figure 5:
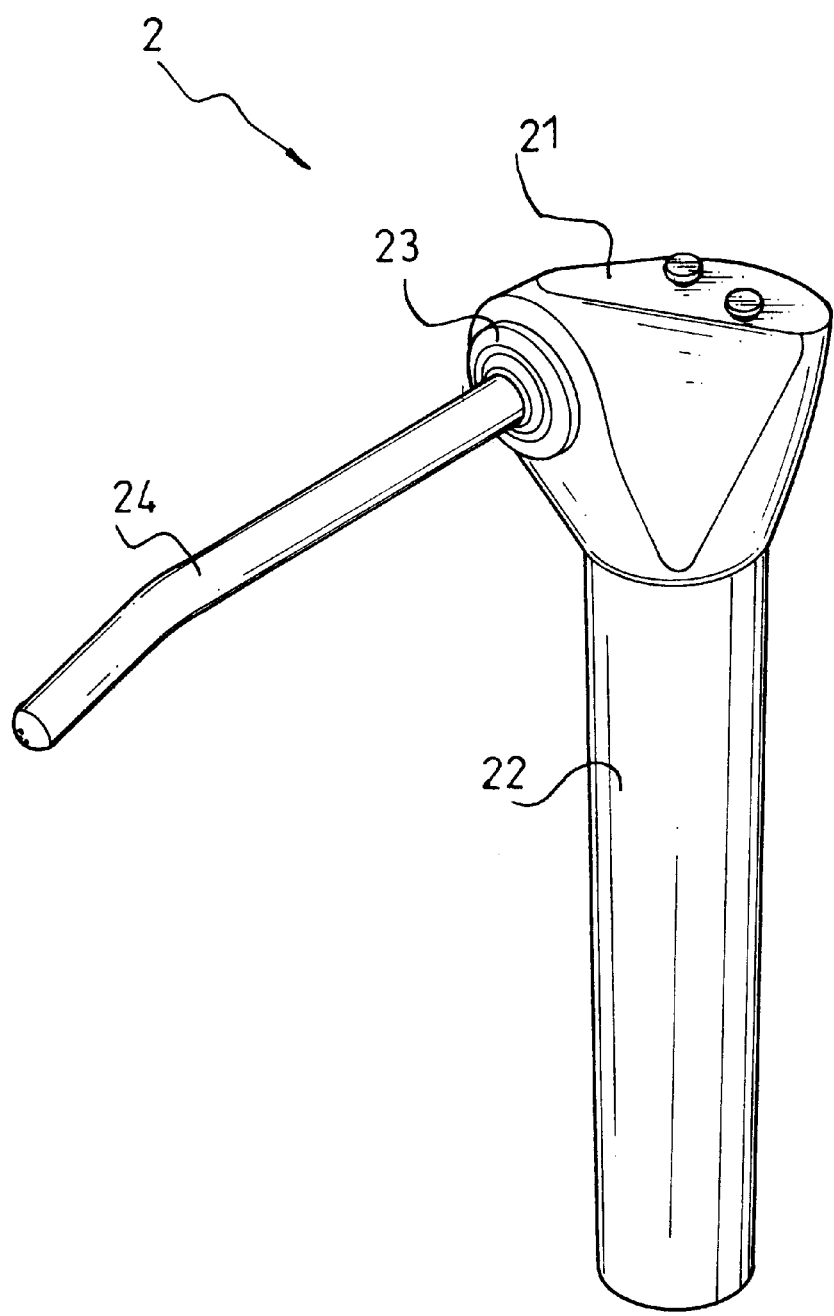
FIG. 5 is a perspective view of a conventional dental syringe for dentists; and, FIG. 6 is an exploded view of the conventional dental syringe shown in FIG. 5.
Figure 6:
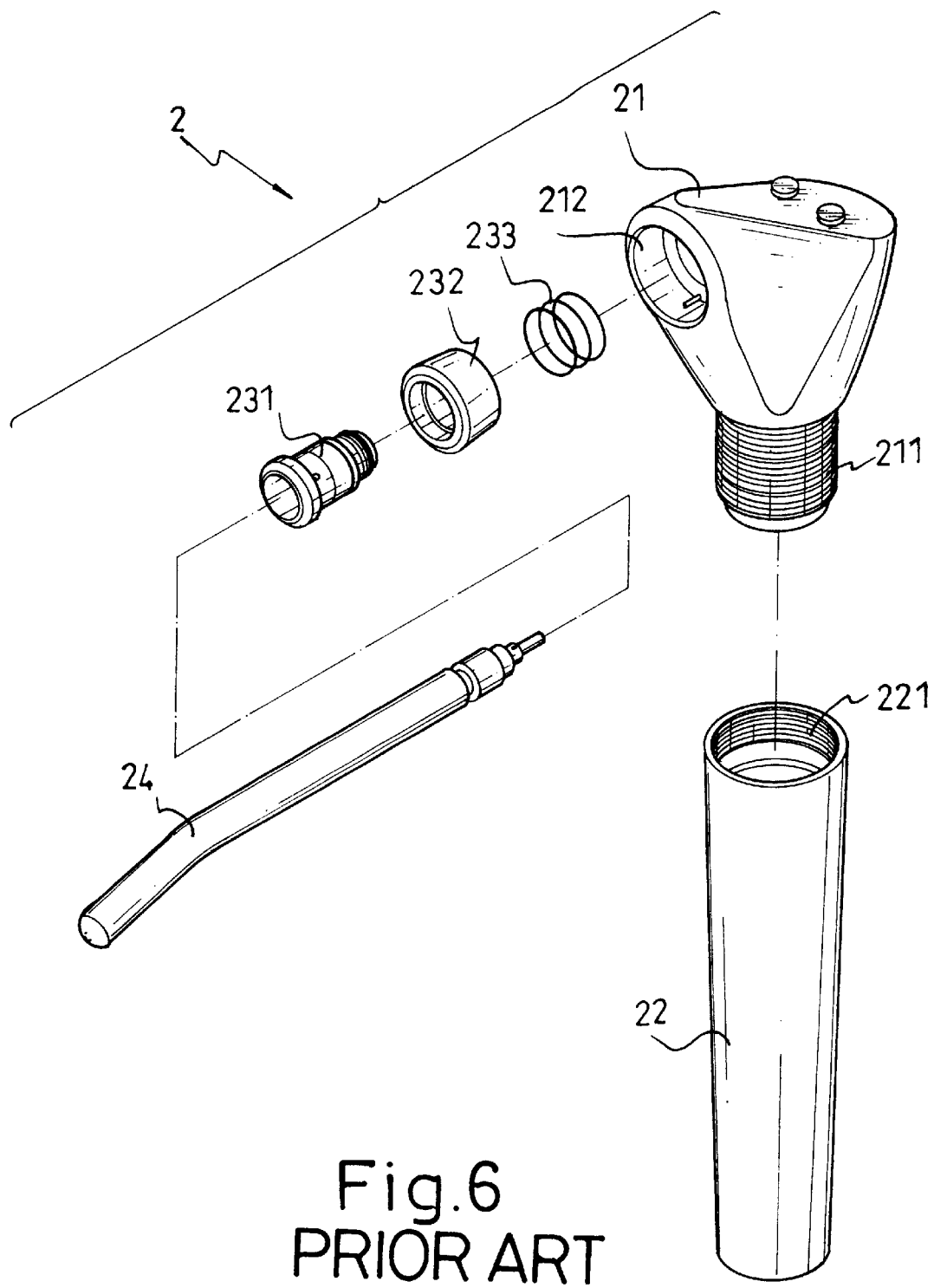

In the insertion of the nozzle (17), the nib (174) will be allowed to extend through the central bottom opening (151) but another portion of the nozzle (17) with a diameter larger than the nib (174) will not. When the inner barrel (15) is pushed inward and no longer blocks the balls (136), the balls (136) are pushed inward by the transition portion (143) under the force of the spring (146). The spring (146) pushes the outer barrel (14) outward until the transition portion (143) is blocked by the front outer flange (134) of the front tube (13), as shown in FIG. 4.

To remove the nozzle (17), a user can push the outer barrel (14) inward against the spring (146). When the inner surface of the outer barrel (14) no longer blocks the balls (136), the balls (136) are pushed outward by the front rim (151) of the inner barrel (15) under the force of the spring (156). The spring (156) pushes the inner barrel (15) outward until it resumes the status as shown in FIG. 3. The engagement between the balls (163) and the circular groove (172) of the nozzle (17) is released and the nozzle (17) is pulled out.

A sealing ring (16) is provided to prevent leakage in the water channel (114) and can surround the nozzle (17).

The invention has following advantages:

1. in both installation and removal of the nozzle (17) from the dental syringe (1), a user can grasp the handle (18) of the dental syringe (1) with one hand and operate it with the other, it is much easier and more convenient than the conventional dental syringe for dentists;
2. the dental syringe will not pinch the user's glove or hand.

What is claimed is:

1. A dental syringe for dentist having: a head (11), a handle (18) securely affixed on the head (11), holding means (111) installed in an opening (110) defined in the head (11), a nozzle (17) being able to be inserted into the holding means (111), and a button (118) for operation, wherein the improvements comprising:

a threaded hole (112) defined in the bottom of the opening (110), and being in communication with a water channel (114) preset in the head (11), an air vent defined in the side wall of the opening (110), a rear tube (12) having:
  a rear male thread (120) defined thereon and engaging with the threaded hole (112),
  a front female thread (122),
  a side air vent (126),
  a bottom opening the diameter of which is smaller than the inner diameter of the rear tube (12), a front tube (13) having:
  a rear male thread (130) engaging with the front female thread (122) of the rear tube (12),
  a front outer flange (134),
  a front inner flange (135),
  a plurality of ball sockets (132) defined in the wall of the front tube (13) axially behind the outer and the inner flange (134, 135),
  one ball (136) put in every ball socket (132);

an outer barrel (14) covering on the front and the rear tube (13, 12) and having:
  a front mouth the diameter of which is slightly larger than the inner diameter of the outer barrel (14) and the front outer flange (134) of the front tube (13),
  a spring (146) pressed between the bottom of the outer barrel (14) and the bottom of the opening (110),
  an axial direction groove (140) defined in the outer surface of the outer barrel (14) for slidably containing a direction bar (144) formed on the bottom of the opening (110) therein to ensure that the outer barrel (14) is only be able to move along the axial of the opening (110);

an inner barrel (15) slidably contained in the front and the rear tube (13, 12) and having:
  a central bottom opening (151) the diameter of which can just allow the passing through of a nib (174) of the nozzle (17),
  a spring (156) pressed between the respective bottoms of the inner barrel (15) and the rear tube (12);

the nozzle (17) having:

a circular groove (172),
the nib (174) the diameter of which is smaller than the nozzle (17) itself,
an air vent (176) defined in the wall of the nozzle (17) and locates between the circular groove (172) and the nib (174).

2. The dental syringe for dentist as claimed in claim 1 wherein an axial direction groove (140) is defined in the outer surface of the outer barrel (14) for slidably containing a direction bar (144) formed on the bottom of the opening (110) to ensure that the outer barrel (14) is only able to move along the axial of the opening (110).

3. The dental syringe for dentist as claimed in claim 1 wherein a sealing ring (138) is provided between the rear tube (12) and the bottom of the opening (110).

4. The dental syringe for dentist as claimed in claim 1 wherein a sealing ring (16) is provided in the water channel (114).

5. The dental syringe for dentist as claimed in claim 1 wherein the small barrel (15) has an outer sealing ring (152) and an inner sealing ring (154).

* * * * *